United States Patent [19]

Okuda et al.

[11] Patent Number: 4,876,407
[45] Date of Patent: Oct. 24, 1989

[54] PROCESS FOR PRODUCING 2,3 DICHLOROBUTADIENE-1,3

[75] Inventors: Akihiko Okuda; Yukinori Totake; Hideki Matsumura, all of Ohmi, Japan

[73] Assignee: Denki Kagaku Kogyo Kabushiki Kaisha, Tokyo, Japan

[21] Appl. No.: 743,273

[22] Filed: Jun. 11, 1985

Related U.S. Application Data

[63] Continuation of Ser. No. 527,507, Aug. 29, 1983, abandoned, which is a continuation of Ser. No. 318,407, Nov. 5, 1981, abandoned.

[30] Foreign Application Priority Data

Nov. 27, 1980 [JP] Japan ................................ 55-166970

[51] Int. Cl.$^4$ ...................... C07C 17/24; C07C 17/34; C07C 21/20
[52] U.S. Cl. .................................................. 570/239
[58] Field of Search .......................... 570/229

[56] References Cited

U.S. PATENT DOCUMENTS

| 1,965,369 | 7/1934 | Carothers et al. | 260/6 |
| 2,445,738 | 7/1948 | Willert | 570/229 |
| 3,898,294 | 8/1975 | Cooley | 570/229 |
| 3,978,146 | 8/1976 | Ohorodnik et al. | 570/229 |
| 3,992,461 | 11/1976 | Kadowacki et al. | 570/229 |
| 4,035,429 | 7/1977 | Karapetian et al. | 570/229 |
| 4,215,708 | 7/1980 | Hargreaves et al. | 570/229 |

FOREIGN PATENT DOCUMENTS

| 53-6124 | 4/1978 | Japan. |
| 946014 | 1/1964 | United Kingdom. |
| 1283651 | 8/1972 | United Kingdom. |

Primary Examiner—J. E. Evans
Attorney, Agent, or Firm—Oblon, Spivak, McClelland, Maier & Neustadt

[57] ABSTRACT 2,3-Dichlorobutadiene-1,3 is produced by a continuous dehydrochlorination of 1,2,3-trichlorobutene-3 in a water miscible solvent in the presence of an alkali metal hydroxide. An evaporator is connected in the downstream of a reactor for the dehydrochlorination to recover the unreacted 1,2,3-trichlorobutene-3 and said water miscible solvent by an evaporation.

11 Claims, 1 Drawing Sheet

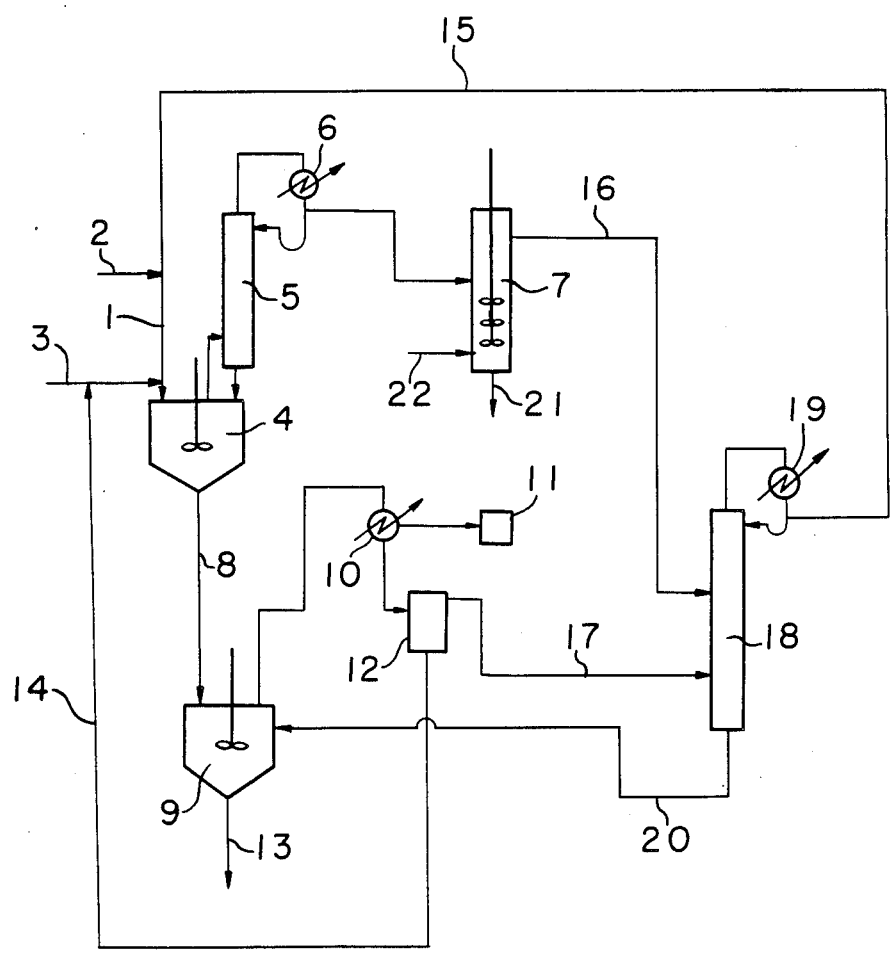

PROCESS FOR PRODUCING 2,3 DICHLOROBUTADIENE-1,3

This application is a continuation of application Ser. No. 527,507, filed Aug. 29, 1983, now abandoned, which in turn is a continuation of application Ser. No. 318,407, filed Nov. 5, 1981, now abandoned.

BACKGROUND OF THE INVENTION

1. Field of the Invention

The present invention relates to a process for producing 2,3-dichlorobutadiene-1,3. More particularly, it relates to a process for producing 2,3-dichlorobutadiene-1,3 at high yield under the condition reducing a formation of polymerized products and reducing an amount of discharged organic materials of a solvent and chlorinated compounds in a drainage.

2. Description of the Prior Art

The process for producing 2,3-dichlorobutadiene-1,3 by a dehydrochlorination of 1,2,3-trichlorobutene-3 in a low boiling point water miscible polar solvent such as methanol in the presence of a base has been disclosed in (1) British Patent No. 946,014; and (2) Japanese Examined Patent Publication No. 6124/1978.

In the process (1), the reaction is carried out at ratios of methanol: sodium hydroxide: water of 75–90:10–5:15–5 by weight and at a molar ratio of sodium hydroxide to 1,2,3-trichlorobutene-3 of 0.7 to 1.0 at 40°–100° C. for a residence time of 3 minutes or shorter with stirring the mixture and the reaction mixture was stripped with steam and the vapor phase is cooled to recover 2,3-dichlorobutadiene-1,3 and the liquid phase is distilled to recover methanol. The conversion is in a range of 70 to 96% and the reaction yield is in a range of 82 to 87%. The reaction yield means a molar percent of the resulting 2,3-dichlorobutadiene-1,3 to the reacted 1,2,3-trichlorobutene-3.

In accordance with this process, the following disadvantages are found. The concentration of methanol should be high. The 2,3-dichlorobutadiene-1,3 polymer is easily formed by the heating in the step of stripping the reaction mixture with steam, to cause a short operation term. The conversion is low to remain a large amount of the unreacted 1,2,3-trichlorobutene-3. The reaction yield is not high. The drainage of the aqueous solution of sodium chloride contains a large amount of organic materials such as methanol and chlorinated compounds.

In the process (2), the reaction is continuously carried out at ratios of water miscible solvent:sodium hydroxide:water of 50–35:10–5:40–60 by weight and at a molar ratio of sodium hydroxide to 1,2,3-trichlorobutene-3 of 1.0 to 1.2 under the atmospheric pressure at 90°–100° C. The reaction mixture in the vapor phase is fed into a distillation column to separate the unreacted 1,2,3-trichlorobutene-3 and the solvent is extracted with water to recycle it into a reactor. The conversion is about 100% and the reaction yield is in a range of 88–91%.

In accordance with the process, the concentration of the solvent in the reaction mixture is not high and the conversion of 1,2,3-trichlorobutene-3 and the reaction yield are high. However, the following disadvantages are found. The reactor is heated at high temperature as 90° to 100° C. Excess alkali is remained because of the molar ratio of sodium hydroxide to 1,2,3-trichlorobutene-3 of more than 1. The polymer material causes fouling the reactor and plugging distillation column which results in short operation term as about 1 week. In order to prolong the life of the operation, it is necessary to reduce the molar ratio of the base or to decrease the reaction temperature. The contamination of the drainage with the unreacted 1,2,3-trichlorobutene-3 and the solvent is increased to reduce the yield and to increase the organic materials in the drainage.

SUMMARY OF THE INVENTION

It is an object of the present invention to overcome the aforementioned disadvantages in the processes (1) and (2) and to provide an industrially advantageous process for not only producing 2,3-dichlorobutadiene-1,3 at high yield without any fouling and/or plugging caused by a polymerization but also reducing an amount of organic materials in a drainage.

The foregoing and other objects of the present invention have been attained by producing 2,3-dichlorobutadiene-1,3 by a continuous dehydrochlorination of 1,2,3-trichlorobutene-3 in the mixture of the starting material, the water miscible solvent, the alkali metal hydroxide and water wherein an evaporator is connected to a reactor for the dehydrochlorination to recover the unreacted 1,2,3-trichlorobutene-3- and the water miscible solvent by an evaporation immediately.

BRIEF DESCRIPTION OF THE DRAWING

FIG. 1 is a flow diagram of one embodiment of the process of the present invention.

DETAILED DESCRIPTION OF THE PREFERRED EMBODIMENTS

In the preferable process for producing 2,3-dichlorobutadiene-1,3 of the present invention, the continuous reaction of 1,2,3-trichlorobutene-3 is carried out in the mixture of the starting material, a water miscible solvent, an alkali metal hydroxide and water in a reactor and the resulting 2,3-dichlorobutadiene-1,3 is immediately evaporated together with a most of the water miscible solvent, a part of the unreacted 1,2,3-trichlorobutene-3 and water to discharge them in a vapor phase and the vapor in a vapor phase is fed into a distillation column to distillate 2,3-dichlorobutadiene-1,3 and the water miscible solvent from the top, and the distillate is extracted with water to separate 2,3-dichlorobutadiene-1,3 and the water miscible solvent and at least 1,2,3-trichlorobutene-3 of the solution discharged from the bottom is recycled into the reactor. On the other hand, the solution of the unreacted 1,2,3-trichlorobutene-3, the water miscible solvent, the alkali metal chloride and water obtained from the reactor is fed into the evaporator to evaporate the unreacted 1,2,3-trichlorobutene-3 and the water miscible solvent and to condense them and the condensate is separated into an upper layer and a lower layer and the lower layer of 1,2,3-trichlorobutene-3 as the main component is recycled into the reactor and the upper layer of the water miscible solvent as the main component is fed together with the water miscible solvent extracted with water, into the distillation column and the water miscible solvent distilled from the top is recycled into the reactor.

In the present invention, an evaporator is connected downstream of the reactor for the dehydrochlorination of 1,2,3-trichlorobutene-3. The reactor is preferably equipped with a stirrer. When the solution discharged from the reactor is evaporated, it is preferable to evaporate it under a reduced pressure in the evaporator.

The water miscible solvents used in the process of the present invention are solvents having a boiling point lower than the boiling point of 2,3-dichlorobutadiene-1,3 (98° C.) such as methanol, ethanol, acetone, isopropanol and t-butanol. In the case of methanol, an azeotropic mixture of 2,3-dichlorobutadiene-1,3 is formed to immediately evapoate it from the reactor after the formation to distill from the top of the distillator. Therefore, it is optimum to use methanol.

It is preferable to use sodium hydroxide as the alkali metal hydroxide used in the dehydrochlorination though the other alkali metal hydroxides can be used.

The dehydrochlorination is usually carried out under the atmospheric pressure and also can be carried out under a reduced pressure or higher pressure.

In the reactor for dehydrochlorination, the ratios of the water miscible solvent:the alkali metal hydroxide:-water are in a range of 50–35:10–5:40–60 by weight. The reaction of 1,2,3-trichlorobutene-3 with the mixture is continuously carried out.

The resulting 2,3-dichlorobutadiene-1,3 is easily polymerized at high temperature in the presence of a base. In the reactor, it is important to keep the molar ratio of the alkali metal hydroxide to 1,2,3-trichlorobutene-3 in 1.0 or less such as 0.9–1.0 to prevent excess alkali in the reaction mixture so as to prevent the polymerization.

The reaction temperature is preferably in a range of 90° to 100° C. so as to rapidly transfer the resulting 2,3-dichlorobutadiene-1,3 out of the reaction system.

It is preferable to add a stabilizer. Ammonium nitrosophenylhydroxylamine is especially effective in the system. The separation is preferably carried out in the presence of this stabilizer. An amount of the stabilizer is enough to be 0.1 to 1 wt. % based on 2,3-dichlorobutadiene-1,3.

Under the condition, it is possible to continue the operation for one month or longer because a polymer material seldom forms in the reactor or the distillation column. The solution discharged from the reactor under the condition contains the unreacted 1,2,3-trichlorobutene-3 at a ratio of 15 to 20% based on the total starting material and so contain portions of the water miscible solvent and the other chlorine compounds. In order to recover these components, it is necessary to connect the evaporator as the feature of the present invention. In order to recover these components under the atmospheric pressure, it is necessary to maintain the temperature of the evaporator at 100° C. higher, thereby causing the trouble of the plugging of the polymer at high temperature. When the pressure is reduced to decrease the temperature for the evaporation, the recovery rate is increased and the stop of the operation caused by the polymerization and the plugging can be prevented, to be able to continue the operation for 1 month or longer. In view of a vacuum device and a condensation temperature, it is preferable to give condition of a pressure of 200 to 300 mmHg (abs.) and a temperature of 80° to 90° C. Under such condition, the vacuum device and the condenser can be small size and water at the ambient temperature can be used as a coolant.

The evaporated vapor is condensed and settled to result in the phase separation into two layers. The lower layer is an oily layer of 1,2,3-trichlorobutene-3 as the main component. The upper layer is a solution of the water miscible solvent. The oily layer has a formulation of 65 to 70 wt. % of 1,2,3-trichlorobutene-3; 10 to 15 wt. % of 1,2,3,3-tetrachlorobutane; 5 to 10 wt. % of a partially reacted 2,3-dichlorobutadiene-1; and 5 to 20 wt. % of the other components. An amount of the lower layer is usually in a range of 15 to 20 wt. % based on the feed of the starting material 1,2,3-trichlorobutene-3. The purity of 1,2,3-trichlorobutene-3 is high thereby recycling it into the reactor.

The concentration of the water miscible solvent in the aqueous solution of the upper layer is in a range of 5 to 10 wt. %. The aqueous solution is fed together with the former aqueous solution of the water miscible solvent into the distillation column to distill the water miscible solvent from the top. The concentrated aqueous solution of the water miscible solvent is recycled into the reactor. The concentration of the water miscible solvent distilled from the top is selected depending upon a concentration of the alkali metal hydroxide in the aqeous solution fed. For example, the concentration of methanol distilled from the top can be about 80% when methanol is used and sodium hydroxide is used as 21% aqueous solution of sodium hydroxide.

When the lower layer and the upper layer are recycled into the reactor to reuse them, loss of chlorinated compounds of 1,2,3-trichlorobutene-3 as the main components and the water miscible solvent is minimized only to the components contained in the solution discharged from the vacuum evaporator. The loss of the components can be less than ⅓ of the loss in the conventional process as disclosed in Japanese Examined Patent Publication No. 6124/1978. The solution discharged from the condenser for the water miscible solvent is a hot water at 100° to 102° C. and accordingly, it can be recycled into the vacuum evaporator in order to utilize the heat energy.

In accordance with the present invention, the vacuum evaporator and the solvent recovery column are connected and if necessary, ammonium nitrosophenylhydroxylamine is added as a stabilizer whereby 2,3-dichlorobutadiene-1,3 can be produced at high yield and the continuous operation term can be prolonged for two to five times and the loss of the solvent and the chlorinated compounds in the drainage can be reduced to less than ⅓ in comparison with the conventional process.

The present invention will be further illustrated by certain examples and references which are provided for purposes of illustration only and are not intended to be limiting the present invention.

EXAMPLE

In the example, methanol is used as the water miscible solvent and sodium hydroxide is used as the alkali metal hydroxide. The process can be carried out by using the other water miscible solvent and the other alkali metal hydroxide.

In the drawing, the reference (1) designates a pipe for feeding a mixture of methanol, sodium hydroxide and water; (2) designates a pipe for feeding sodium hydroxide, water and a supplemental methanol; (3) designates a pipe for feeding 1,2,3-trichlorobutene-3 as the starting material; (4) designates an atmospheric pressure reactor equipped with stirrer; (5) designates a distillation tower for the unreacted 1,2,3-trichlorobutene-3; (6) designates a condenser; (7) designates an extraction tower; (8) designates a pipe for discharging a solution discharged from the atmospheric pressure reactor; (9) designates a vacuum evaporator equipped with a stirrer; (10) designates a condenser; (11) designates a vacuum device; (12) designates a settler separator; (13) designates a pipe for discharging a solution discharged from said vacuum evaporator; (14) designates a pipe for recycling the recovered 1,2,3-trichlorobutene-3; (15) designates a pipe for recycling methanol-water; (16) designates a pipe for feeding methanol-water; (17) designates a pipe for feeding methanolwater; (18) designates a methanol concentration tower; (19) designates a condenser; (20) designates a pipe for returning hot water; (21) designates a pipe for recovering a mixture of the resulting 2,3-dichlorobutadiene-1,3 and a portion of 1,2,3-trichlorobutene-3; and (22) designates a pipe for feeding water.

The mixture of methanol, sodium hydroxide and water is fed through the pipe (1) and 1,2,3-trichlorobutene-3 is continuously fed through the pipe (3) together with 1,2,3-trichlorobutene-3 fed through the pipe (14) into the reactor (4). The rates of the components fed per unit time are as follows:

| 1,2,3-trichlorobutene-3 (purity of 90%): | 150 wt. parts |
| Methanol: | 165 wt. parts |
| Sodium hydroxide: | 36 wt. parts |
| Water: | 180 wt. parts |

The reaction is carried out at a reaction temperature of 92° C. under the atmospheric pressure, whereby the resulting 2,3-dichlorobutene-1,3, methanol, the unreacted 1,2,3-trichlorobutene-3 and water are evaporated from the reactor (4). The vapor is fed into distillation tower for separating the unreacted 1,2,3-trichlorobutene-3. The temperature of the top of the distillation tower (5) is kept at 64° C. as the azeotropic temperature of the azeotropic mixture of 2,3-dichlorobutadiene-1,3 and methanol. The mixed vapor is distilled from the distillation tower (5) as the azeotropic mixture of about 35 wt. % of 2,3-dichlorobutadiene-1,3 and about 65 wt. % of methanol from the top and 1,2,3-tichlorobutene-3 is discharged from the bottom. The solution discharged from the bottom is recycled into the reactor (4). The azeotropic mixture of 2,3-dichlorobutadiene-1 and methanol distilled from the top may be contaminated with small amounts of 1,2,3-trichlorobutene-3 and the high boiling material. The mixture is condensed by the condenser (6) and then, methanol is extracted with water in the extractor (7) and the extracted methanol is discharged from the top and recycled through the pipe (16) together with the solution fed through the pipe (17) into the recycling system. The solution discharged from the bottom of the extractor (7) has for example, the formulation:
2,3-dichlorobutadiene-1,3: about 90 wt. %;
1,2,3-trichlorobutene-3: about 5 wt. %;
high boiling materials: about 5 wt. %;
The main component is 2,3-dichlorobutadiene-1,3.

The mixture is fed from the pipe (21) into a distillation tower (the shown) to obtain 2,3-dichlorobutadiene-1 from the top and 1,2,3-trichlorobutene-3,2,3-dichlorobutadiene-1,3 and high boiling materials are discharged from the bottom and recycled into the reactor (4).

At the same time for the evaporation from the reactor (4), the unreacted 1,2,3-trichlorobutene-3, methanol, sodium chloride and water are discharged from the reactor (4) through the pipe (8) and are continuously fed into the vacuum evaporator (9) in which the pressure is kept under 200 mmHg (abs.) and the temperature is kept at 82° C. to evaporate 1,2,3-trichlorobutene-3 and methanol and mixed vapor is condensed by the condenser (10) and the condensate is settled into two layers in the settler separator (12). The upper layer is methanol-water (8 wt. % of methanol) and the lower layer is an oily layer containing 70 wt. % of 1,2,3-trichlorobutene-3 at a rate of 19 wt. % based on the total feed of the starting materials. The lower layer is recycled into the reactor (1). The upper layer is mixed with the solution fed through the pipe (16) and the mixture is fed through the pipe (17) to concentrate methanol by the methanol concentration column (18) and methanol distilled from the top is balanced with water at a concentration of 80% and is recycled into the reactor (9). A temperature of hot water discharged from the bottom is 102° C. and accordingly, the heat energy is recovered by recycling the hot water through the pipe (20) into the vacuum evaporator (9). The solution discharged from the bottom of the vacuum evaporator (9) is an aqueous solution of sodium chloride and a loss of organic compounds is quite small.

Thus, 105 wt. parts of 2,3-dichlorobutadiene-1,3 is obtained at yield of 91%.

In the vacuum evaporator, a dehydrochlorination of the unreacted 1,2,3-trichlorobutene-3 is partially performed to produce 2,3-dichlorobutadiene-1,3. The residence time in the evaporator is preferably in a range of 0.5 to 1 hour in view of the increase of the yield. A trouble of the polymerization and clogging can be substantially prevented when the solution is well stirred and recycled. The upper layer separated by settling in the settler separator (12) has the formulation of 20 wt. parts of methanol and 230 wt. parts of water. The lower layer has the formulation of 20 wt. parts of 1,2,3-trichlorobutene-3, 2 wt. parts of 2,3-dichlorobutadiene-1,3, 3 wt. parts of 1,2,3,3-tetrachlorobutane and 3 wt. parts of the other components.

The upper layer is mixed with the methanol-water discharged from the extractor (7) and methanol is concentrated in the concentration tower (18) and is recycled into the reactor (4). In order to prevent the polymerization, 0.4 wt. % of ammonium nitrosophenylhydroxylamine as 2.5% methanol solution is fed as the stabilizer into the top of the distillation tower (5), the reactor (4) and the condenser (6).

In the reactor (4), the distillation tower (5) for separating the unreacted 1,2,3-trichlorobutene-3, the condenser (6), the vacuum evaporator (9), the condenser (10), the settler separator (12), the methanol concentration tower (18) and the condenser (19), any plugging of the polymerized product for stop of the operation is not found to be capable of a continuous operation for 1 month or longer. The recovery rate of methanol is 95% under said condition and can be further improved by selecting suitable temperature and pressure.

The amounts of methanol and the chlorinated compounds in the drainage can be reduced to ⅓ or less in comparison with the conventional process disclosed in Japanese Examined Patent Publication No. 6124/1978.

We claim:

1. A process for producing 2,3-dichlorobutadiene-1,3 which comprises (i) continuously reacting a mixture of 1,2,3-trichlorobutene-3, a water miscible solvent, an alkali metal hydroxide and water in a reactor; (ii) discharging the resulting 2,3-dichlorobutadiene-1,3, most of said water miscible solvent and a part of the unreacted 1,2,3-trichlorobutene-3 and water in a vapor phase from said reactor by evaporation just after the reaction; (iii) feeding said vapor phase into a distillation column to distillate 2,3-dichlorobutadiene-1,3 and said water miscible solvent from the top; (iv) extracting the distillate with water to separate 2,3-dichlorobutadiene-1,3 from said water miscible solvent; (v) recycling at least 1,2,3-trichlorobutene-3 solution discharged from the bottom, into said reactor; (vi) feeding a mixture of the unreacted 1,2,3-trichlorobutene-3, said water miscible solvent and alkali metal chloride and water discharged from said reactor, into an evaporator to evaporate the unreacted 1,2,3-trichlorobutene-3 and said water miscible solvent; (vii) condensing said vapor into an upper layer and a lower layer condensate; (viii) recycling said lower layer condensate containing mainly 1,2,3-trichlorobutene-3, into said reactor; (ix) feeding said upper layer condensate containing said water miscible solvent and said water miscible solvent extracted with water in step (iv) into a methanol concentration tower; and (x) recycling said water miscible solvent distilled from the top, into said reactor.

2. In a process for producing 2,3-dichlorobutadiene-1,3 by the continuous dehydrochlorination of 1,2,3-trichlorobutene-3 in a water miscible solvent and water in the presence of an alkali metal hydroxide in a reactor and withdrawal, from said reactor, of vapor containing product 2,3-dichlorobutadiene-1,3 among other materials from said reaction, said product 2,3-dichlorobutadiene-1,3 being separated from the 1,2,3-trichlorobutene-3 by distillation in a distillation column, the improvement comprising:

(a) carrying out the dehydrochlorination at an alkali metal hydroxide to 1,2,3-trichlorobutene-3 molar ratio of less than about 1.0;

(b) using water miscible solvent: alkali metal hydroxide: water weight ratio in the ranges of 50–35:-10–5:40–60;

(c) feeding a liquid portion of said reaction mixture to an evaporator connected to said reactor;

(d) evaporating the liquid portion comprising 1,2,3-trichlorobutene-3 and water miscible solvent from said reactor;

(e) condensing the vaporous mixture;

(f) recycling the 1,2,3-trichlorobutene-3 to the reactor;

(g) recovering the water miscible solvent.

3. The process of claim 2, wherein said evaporation is carried out under reduced pressure.

4. The process of claim 2, wherein said evaporation is carried out in an evaporator with a stirrer.

5. The process of claim 2, wherein said improvement further comprises that the dehydrochlorination and said evaporation are carried out in the presence of a stabilizer.

6. The process of claim 5, wherein said stabilizer is ammonium nitrosophenylhydroxylamine.

7. The process of claim 2, wherein said recovered water miscible solvent is concentrated.

8. The process of claim 7, wherein said concentrated water miscible solvent is recycled into said reactor.

9. The process of claim 2, wherein said improvement further comprises that the dehydrochlorination is carried out at a temperature of 90° to 100° C.

10. The process of claim 2, wherein said improvement further comprises that the water miscible solvent is methanol.

11. The process of claim 2, wherein said improvement further comprises that the alkali metal hydroxide is sodium hydroxide.

* * * * *